United States Patent
Adams et al.

(10) Patent No.: US 10,537,563 B2
(45) Date of Patent: Jan. 21, 2020

(54) METHODS FOR TREATING OCULAR DISEASE USING INHIBITORS OF CSF-1R

(71) Applicant: NOVARTIS AG, Basel (CH)

(72) Inventors: Christopher Adams, Arlington, MA (US); Muneto Mogi, Waltham, MA (US); Stephen Hedrick Poor, Winthrop, MA (US); Timothy Michael Ramsey, Weston, MA (US); Henry Wu, Boston, MA (US); Qin Zhang, Winchester, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/341,075

(22) PCT Filed: Oct. 13, 2017

(86) PCT No.: PCT/IB2017/056380
§ 371 (c)(1),
(2) Date: Apr. 11, 2019

(87) PCT Pub. No.: WO2018/069893
PCT Pub. Date: Apr. 19, 2018

(65) Prior Publication Data
US 2019/0231765 A1    Aug. 1, 2019

Related U.S. Application Data

(60) Provisional application No. 62/408,345, filed on Oct. 14, 2016.

(51) Int. Cl.
*A61K 31/4427* (2006.01)
*A61K 31/4439* (2006.01)
*A61P 27/02* (2006.01)
*A61K 9/00* (2006.01)

(52) U.S. Cl.
CPC ........ *A61K 31/4439* (2013.01); *A61K 9/0048* (2013.01); *A61K 9/0053* (2013.01); *A61P 27/02* (2018.01)

(58) Field of Classification Search
CPC .................................. A61K 31/4427
USPC .......................................... 514/338
See application file for complete search history.

(56) References Cited

U.S. PATENT DOCUMENTS

2014/0065141 A1 * 3/2014 Daniel ............... A61K 31/4439
424/133.1

FOREIGN PATENT DOCUMENTS

EP        2 186 529 A2    5/2010
WO      2012/151523 A1    11/2012

OTHER PUBLICATIONS

Kubota, Y. et al.: "M-CSF inhibition selectively targets pathological angiogenesis and lymphangiogenesis", Journal of Clinical Investigation, vol. 118, No. 7, Apr. 27, 2009, pp. 1089-1102.
Wei, Liu et al.: "Macrophage colony-stimulating factor and its receptor signaling augment glycated albumin-induced retinal microglial inflammation in vitro", BMC Cell Biology, Biomed Central, London, vol. 12, No. 1, Jan. 25, 2011, p. 5.

* cited by examiner

*Primary Examiner* — Raymond J Henley, III
(74) *Attorney, Agent, or Firm* — Asha K. Nadipuram

(57) ABSTRACT

The present invention provides in one aspect methods for treating ocular diseases by administering pharmaceutical compositions comprising an inhibitor of colony stimulating factor-1 (CSF-1) receptors. In another aspect, the present invention provides pharmaceutical compositions for treating ocular diseases, the compositions comprising at least one inhibitor of CSF-1R. The inhibitor can also be a selective inhibitor of CSF-1R in certain embodiments.

19 Claims, 4 Drawing Sheets

METHODS FOR TREATING OCULAR DISEASE USING INHIBITORS OF CSF-1R

RELATED APPLICATIONS

This application is a National Stage of International Application PCT/IB2017/056380, filed Oct. 13, 2017, which claims priority to, and the benefit of, U.S. provisional application No. 62/408,345, filed Oct. 14, 2016, the entire contents of which are incorporated herein by reference in their entirety.

FIELD OF THE INVENTION

The present invention relates to methods and pharmaceutical compositions for treating ocular diseases using inhibitors of colony stimulating factor 1 receptor (CSF-1R).

BACKGROUND OF THE INVENTION

Colony stimulating factor 1 (CSF-1) is a secreted cytokine which is a regulator of the production, differentiation, and function of macrophages, monocytes, and other hematopoietic precursor cells. The encoded CSF-1 receptor (CSF-1R) protein is a tyrosine kinase transmembrane receptor and member of the CSF1/PDGF receptor family of tyrosine-protein kinases. Binding of CSF-1 to CSF-1R induces the activation of tyrosine kinase such as PI3K and MEK. The CSF-1 receptor mediates the majority of the biological effects of this cytokine which can include anti-inflammatory activity. CSF-1 receptor inhibition has been theorized to have utility in the treatment of cancer, but was considered unlikely as a therapeutic technique to be effective in the treatment of inflammatory disease (Hume et al. Blood 119: 1810-1820 (2012)).

Vascular endothelial growth factor (VEGF) is a known regulator of angiogenesis and neovascularization, and has been shown to be a key mediator of neovascularization associated with tumors and intraocular disorders (Ferrara et al. Endocr. Rev. 18:4-25 (1997)). The concentration of VEGF in eye fluids are highly correlated to the presence of active proliferation of blood vessels in patients with diabetic and other ischemia-related retinopathies (Berkman et al., J Clin Invest 91:153-159 (1993); Brown et al. Human Pathol. 26:86-91 (1995); Brown et al. Cancer Res. 53:4727-4735 (1993); Mattern et al. Brit. J. Cancer. 73:931-934 (1996); and Dvorak et al. Am J. Pathol. 146:1029-1039 (1995); Aiello et al. N. Engl. J. Med. 331:1480-1487 (1994)). In addition, studies have shown the presence of localized VEGF in choroidal neovascular membranes in patients affected by age-related macular degeneration (AMD) (Lopez et al. Invest. Ophtalmo. Vis. Sci. 37:855-868 (1996)). Several anti-VEGF therapeutics have been developed for the treatment of ocular disorders such as AMD and diabetic retinopathy; such therapeutics include ranibizumab (LUCENTIS®) and aflibercept (EYLEA®).

SUMMARY OF THE INVENTION

The present invention relates to methods and pharmaceutical compositions for treating ocular diseases using antagonists of the CSF-1 receptor.

One aspect of the present invention provides methods and pharmaceutical compositions for treating ocular diseases using selective antagonists of the CSF-1 receptor.

Yet another aspect of the present invention relates to methods and pharmaceutical compositions for treating ocular diseases using Compound (I):

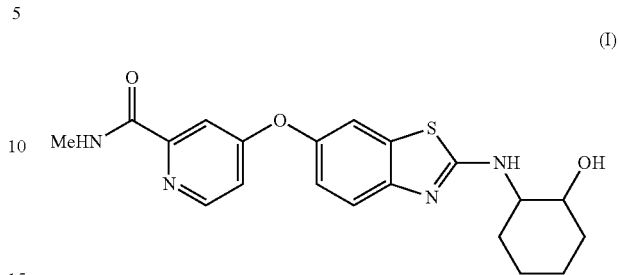

as a non-salt (free base), or a pharmaceutically acceptable salt thereof.

Another aspect of the present invention relates to methods and pharmaceutical compositions for treating neovascular ocular diseases, including but not limited to diabetic retinopathy and age-related macular degeneration.

Specific preferred embodiments of the invention will become evident from the following more detailed description of certain preferred embodiments and the claims.

DETAILED DESCRIPTION

Figure 1:
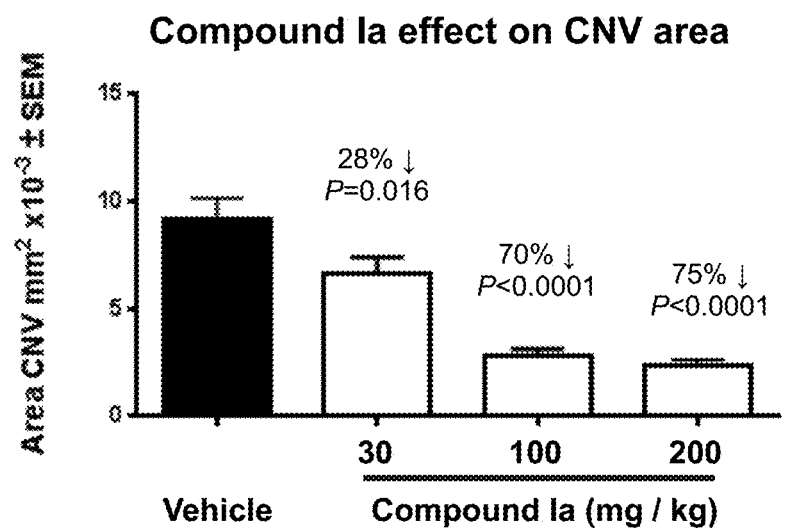
FIG. 1 is a bar graph with neovascularization area data from a rodent CNV model comparing test populations treated with Compound (Ia) against vehicle.

"CSF-1 receptor" or "CSF-1R" is defined as a receptor, having an activity corresponding to the activity of the human CSF-1 receptor subtype. The CSF-1 receptor or CSF-1R (also called c-fms) has been characterized through molecular cloning and pharmacology as detailed in Roussel et al., Nature 325:549-552 (1987).

"CSF-1R inhibitor" refers to a compound that can inhibit colony stimulating factor 1 (CSF-1) receptor. A selective CSF-1R inhibitor has selective inhibition of CSF-1R over vascular endothelial growth factor (VEGF). In a preferred embodiment, such selective inhibition refers to a least a 2:1 binding preference of a compound according to the present disclosure for CSF-1R compared to VEGF, more preferably at least 5:1, and even more preferably at least 10:1.

The language "effective amount" of the compounds described herein, refers to that amount of a therapeutic compound necessary or sufficient to perform its intended function within a mammal, e.g., treat a CSF-1R associated disorder, or a disease state in a mammal. An effective amount of the therapeutic compound can vary according to factors such as the amount of the causative agent already present in the mammal, the age, sex, and weight of the mammal, and the ability of the therapeutic compounds of the present disclosure to affect the CSF-1R associated disorder in the mammal. One of ordinary skill in the art would be able to study the aforementioned factors and make a determination regarding the effective amount of the therapeutic compound without undue experimentation. An in vitro or in vivo assay also can be used to determine an "effective amount" of the therapeutic compounds described herein. The ordinarily skilled artisan would select an appropriate amount of the therapeutic compound for use in the aforementioned assay or as a therapeutic treatment.

The phrase "ophthalmically compatible" is art-recognized and refers to formulations, polymers and other materials and/or dosage forms which are suitable for use in contact with the ocular tissues of human beings and animals without excessive toxicity, irritation, allergic response, or other problem or complication, commensurate with a reasonable benefit/risk ratio as determined by one of ordinary skill in the art.

As used herein, the term "treat", "treating" or "treatment" in connection to a disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

In certain embodiments of the present invention, the compounds of the present disclosure, such as Compounds (I), (Ia) and (Ib), have surprisingly been found not to interact strongly with VEGF at concentrations where the signaling of the CSF-1 receptor is strongly or completely inhibited. Preferably, the compounds of the disclosure are also selective with respect to other tyrosine kinase receptors, such as Syk or CDK receptors.

As used herein, a pharmaceutical composition is a composition suitable for pharmaceutical use. A composition suitable for pharmaceutical use may be sterile, homogeneous and/or isotonic. Pharmaceutical compositions may be prepared in certain embodiments in an aqueous form, for example in a pre-filled syringe or other single- or multi-dose container. In certain embodiments of the invention, the pharmaceutical composition is ophthalmically compatible and suitable for ophthalmic administration to a human subject by, for example, topical or other known methods of delivery. In another embodiment of the invention, the pharmaceutical composition is suitable for intravitreal administration. In yet another embodiment of the invention, the pharmaceutical composition is suitable for administration by intravitreal infusion. In yet another embodiment, the pharmaceutical composition is administered orally.

The present invention provides in certain embodiments novel pharmaceutical formulations, in particular novel pharmaceutical formulations in which the active ingredient comprises Compound (I):

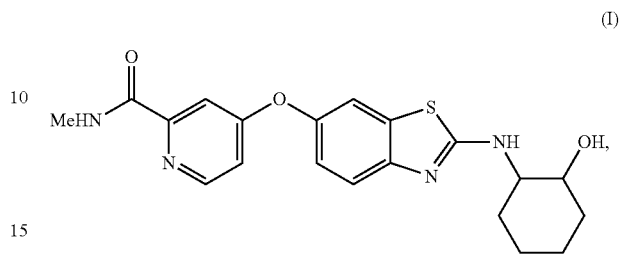

(I)

or a pharmaceutically acceptable salt thereof.

Compound (I) can be synthesized using procedures known in the art and described in WO2007/121484 and U.S. Pat. No. 7,553,854 ("6-O-Substituted Benzoxazole and Benzothiazole Compounds and Methods of Inhibiting CSF-1R Signaling") to Sutton et al., both of which are hereby incorporated by reference in their entireties. Various stereoisomers of Compound (I) may be used, such as 4-((2-(((1R,2R)-2-hydroxycyclohexyl)amino)benzo[d]thiazol-6-yl)oxy)-N-methylpicolinamide (Compound (Ia)) and 4-((2-(((1S,2S)-2-hydroxycyclohexyl)amino)benzo[d]thiazol-6-yl)oxy)-N-methylpicolinamide (Compound (Ib)) with the following structures respectively.

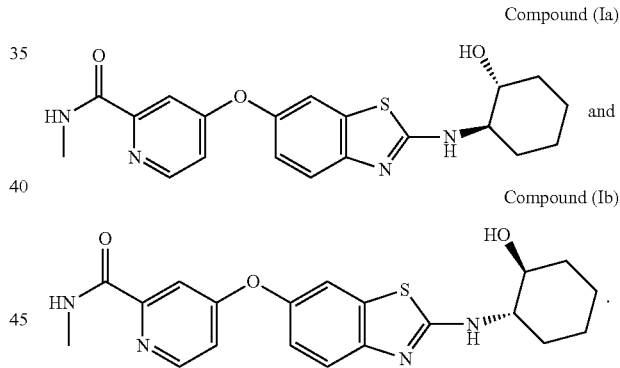

Compound (Ia)

and

Compound (Ib)

Additionally or alternatively, various crystalline and polymorphic forms of Compound (I), (Ia) or (Ib) may be used, Any chemical formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds of the disclosure include, for example, isotopes of hydrogen, carbon, nitrogen, and oxygen, such as $^3H$, $^{11}C$, $^{13}C$, $^{14}C$, and $^{15}N$. Accordingly, it should be understood that methods, composition and combination therapies of the present invention can or may involve compounds that incorporate one or more of any of the aforementioned isotopes, including for example, radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. Isotopically-labeled compounds can generally be prepared by conventional techniques known to those skilled in the art, e.g., using an appropriate isotopically-labeled reagents in place of the non-labeled reagent previously employed.

The present invention encompasses embodiments that include all pharmaceutically acceptable salts of the compounds useful according to the invention provided herein. As used herein, "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts of the parent compound formed, for example, from non-toxic inorganic or organic acids. The pharmaceutically acceptable salts can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, Pa., 1985, p. 1418 and *Journal of Pharmaceutical Science,* 66, 2 (1977), each of which is incorporated herein by reference in its entirety. For example, preferred pharmaceutically acceptable salts include, but are not limited to, mineral or organic acid salts of basic residues such as amines. For example, the salt can be a hydrochloride salt. Other examples of suitable salts can be found in U.S. Pat. No. 7,553,854, the content of which is hereby incorporated by its entirety.

The phrase "pharmaceutically acceptable" as employed herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Compound (I) or a pharmaceutically acceptable salt thereof may be incorporated in various formulations for delivery. For example, topical formulations can be used and can include ophthalmically acceptable preservatives, surfactants, viscosity enhancers, buffers, sodium chloride, and water to form aqueous ophthalmically compatible solutions and suspensions. Systemic formulations (for example, orally ingested tablets) and formulations for intraocular injection are also contemplated. Such systemic formulations include, by way of non-limiting example, oral composition doses comprising from 1 to 1000 mg Compound (I) per dose, 5 to 500 mg Compound (I) per dose, or from 10 to 100 mg Compound (I) per dose.

The specific type of formulation selected will depend on various factors, such as the compound or its salt being used, the dosage frequency, and the location of the disease being treated. Topical ophthalmically compatible aqueous solutions, suspensions, ointments, and gels are the preferred dosage forms for the treatment of ocular diseases in the front of the eye (the cornea, iris, trabecular meshwork); or ocular diseases of the back of the eye if the compound can be formulated such that it can be delivered topically and is able to penetrate the tissues in the front of the eye. Compound (I) will normally be contained in these formulations in an amount from about 0.01% to about 10.0% by weight. Preferable concentrations for topical administration range from about 0.1% to about 5.0% by weight. Thus, for topical administration, these formulations are delivered to the surface of the eye one to six times a day, depending on the routine discretion of the skilled clinician. Systemic administration, for example, in the form of tablets is useful for the treatment of ocular disease particularly of the back of the eye, for example, the retina. Tablets containing, for example 10-500 mg of Compound (I) can be taken once per day or more than once daily (such as 2-3 times per day) depending on the discretion of the skilled clinician.

Unless otherwise specified, the weight or dosage referred to herein for a particular compound (e.g., any of Compounds (I), (Ia), and (Ib)) described herein is the weight or dosage of the compound itself, not that of a salt or prodrug thereof, which can be different to achieve the intended therapeutic effect. For example, the weight or dosage of a corresponding salt of a compound suitable for the methods, compositions, or combinations disclosed herein may be calculated based on the ratio of the molecular weights of the salt and compound itself.

Compounds (I), (Ia), (Ib) and/or pharmaceutically acceptable salts thereof are preferably incorporated into ophthalmically compatible formulations for delivery to the eye. The compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity such as hydroxymethylcellulose, hydroxyethylcellulose, hydroxypropyl methylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle such as mineral oil, liquid lanolin, or white petrolatum. Sterile ophthalmic gel formulations may be prepared by suspending the compound in a hydrophilic base prepared from the combination of, for example, Carbopol®-974, or the like, according to the published formulations for analogous ophthalmic formulations; preservatives and tonicity agents can be incorporated.

The pharmaceutical compositions may include one or more buffering agent(s) or pH adjusting agent(s) to provide improved pH control. In certain topical embodiments of the invention, a pharmaceutical composition has a pH between 5.0 and 8.0, between 5.0 and 7.0, between 6.0 and 8.0, or between 6.0 and 7.0. In one embodiment, the pH of a pharmaceutical composition is about 6.3 to about 7.3. In a specific embodiment, an aqueous pharmaceutical composition of the invention has an approximately neutral pH of about 6.8.

Other contemplated excipients, which may be utilized in the pharmaceutical compositions of the invention include, for example, antimicrobial agents, antioxidants, antistatic agents, lipids such as phospholipids or fatty acids, steroids such as cholesterol, protein excipients such as serum albumin (human serum albumin), recombinant human albumin, gelatin, casein, salt-forming counterions such sodium and the like. These and additional known pharmaceutical excipients and/or additives suitable for use in the formulations of the invention are known in the art, e.g., as listed in "The Handbook of Pharmaceutical Excipients, 4th edition, Rowe et al., Eds., American Pharmaceuticals Association (2003); and Remington: the Science and Practice of Pharmacy, $21^{st}$ edition, Gennaro, Ed., Lippincott Williams & Wilkins (2005).

In another aspect, the present invention provides a pharmaceutical composition comprising a compound of the present disclosure, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

In another embodiment, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and/or sweeteners.

Tablets may be either film coated or enteric coated according to methods known in the art.

Suitable compositions for oral administration include an effective amount of a compound of the disclosure in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Pharmaceutical compositions of the present invention comprising Compound (I) are particularly useful to treat neovascular ocular diseases in a subject.

A "neovascular ocular disease" that can be treated using a pharmaceutical composition of the invention includes, a condition, disease, or disorder associated with ocular neovascularization, including, but not limited to, abnormal angiogenesis, choroidal neovascularization (CNV), retinal vascular permeability, retinal edema, diabetic retinopathy (particularly proliferative diabetic retinopathy), diabetic macular edema, neovascular (exudative) age-related macular degeneration (AMD), including CNV associated with nAMD (neovascular AMD), sequela associated with retinal ischemia, Central Retinal Vein Occlusion (CRVO), and posterior segment neovascularization.

Other ocular diseases may be treated using certain embodiments of the present invention. A non-limiting list of such ocular diseases includes neovascular ocular diseases, polypoidal choroidal vasculopathy, proliferative vitreoretinopathy, anterior segment neovascularization, graft-versus-host disease, ocular tumors, corneal graft rejection, uveitis, geographic atrophy, dry (atrophic) or wet (neovascular or exudative) AMD, glaucoma, and dry eye syndrome (Keratoconjunctivitis Sicca) such as dry eyes resulting from Sjogren's Syndrome.

In dry eye diseases, desiccating stress, factors that disrupt tear film stability, increase tear osmolarity, or any combination thereof can induce ocular surface damage and initiate an inflammatory cascade to activate local macrophages. Macrophages can then exert direct cytotoxicity and/or act as antigen presenting cells to present antigen to and thereby activate local T cells for cytokine release. Without wishing to be bound by theory, regulation of macrophages by Compound (I) or an isolated stereoisomer thereof or a salt thereof can turn off the inflammatory immune response responsible for dry eyes and therefore alleviating or treating dry eye or symptoms thereof.

The pharmaceutical compositions of the invention may include an additional therapeutic agent in addition to Compound (I). Further therapeutic agents may include, for instance, other compounds and antibodies useful for treating ocular diseases. A non-limiting list of such agents comprises bevacizumab, ranibizumab, aflibercept, pegpleranib, pegaptanib, conbercept, squalamine, abicipar pegol, PAN-90806, brolucizumab, and REGN2176-3. Other agents include VEGF-R2 inhibitors disclosed in WO2010066684A2 including but not limited to (S)-5-(6-methyl-5,6,7,8-tetrahydropyrido[3,4-d]pyrimidin-4-yloxy)-N-(5-(1-methylcyclopropyl)-1H-pyrazol-3-yl)-1H-indole-1-carboxamide (Example 54-B), 5-(6,7-dihydro-5H-pyrrolo[3,4 d]pyrimidin-4-yloxy)-indole-1-carboxylic acid [5-(1-methyl-cyclopropyl)-2H-pyrazol-3-yl]-amide (Example 54-O), 5-(5,6,7,8- tetrahydro-pyrido[3,4-d]pyrimidin-4-yloxy)-indole-1-carboxylic acid [5-(1-methyl-cyclopropyl)-2H-pyrazol-3-yl]-amide (Example 54-Q) and N-(1-methyl-5-(trifluoromethyl)-1H-pyrazol-3-yl)-5-((6-((methylamino)methyl)pyrimidin-4-yl)oxy)-1H-indole-1-carboxamide (Example 137-O).

Pharmaceutical compositions of the invention can be administered to a patient. As used herein, the term "subject" or "patient" refers to human and non-human mammals, including but, not limited to, primates, rabbits, pigs, horses, dogs, cats, sheep, and cows. Preferably, a subject or patient is a human. In one embodiment, the term "patient" or "subject" refers to a human being who is diseased with the condition (i.e., disease or disorder) described herein and who would benefit from the treatment. As used herein, a subject is "in need of" a treatment if such subject (patient) would benefit biologically, medically or in quality of life from such treatment.

Various delivery methods for administration of the pharmaceutical compositions are contemplated and may include, for example, topical, intravitreal, oral, intravenous (IV), intracameral, and other methods known to those of skill in the art.

In one embodiment, administration will typically be via a syringe. Thus the invention provides a delivery device (e.g. a syringe) including a pharmaceutical composition of the invention (e.g., pre-filled syringe). The pharmaceutical composition may include an additional therapeutic agent in addition to Compound (I). Patients will receive an effective amount of Compound (I) or a salt thereof as the principal active ingredient.

The invention further provides a method for delivering Compound (I) or a salt thereof to a patient, comprising a step of administering to the patient a pharmaceutical composition of the invention one or more times daily.

Certain specific embodiments of the invention are described as numbered hereafter:

Embodiment 1

A method of treating a mammalian subject having an ocular disease, said method comprising administering to the subject an effective amount of Compound (I) as a non-salt (free base) or a pharmaceutically acceptable salt thereof.

Embodiment 2

A method of treating a mammalian subject having an ocular disease associated with pathological neovascularization, said method comprising administering to the subject an effective amount of Compound (I) as a non-salt or a pharmaceutically acceptable salt thereof.

Embodiment 3

A method of treating a mammalian subject having a retinal disease or retinopathy, said method comprising administering to the subject an effective amount of Compound (I) as a non-salt or a pharmaceutically acceptable salt thereof.

Embodiment 4

A method of treating a mammalian subject having diabetic retinopathy, diabetic macular edema, or age-related macular degeneration, said method comprising administering to the subject an effective amount of Compound (I) as a non-salt or a pharmaceutically acceptable salt thereof.

Embodiment 5

A method of treating a mammalian subject having an ocular disorder, said method comprising administering to the subject an effective amount of Compound (I) as a non-salt or a pharmaceutically acceptable salt thereof, and wherein the ocular disorder is selected from the group consisting of: abnormal angiogenesis, choroidal neovascularization (CNV), retinal vascular permeability, retinal edema, diabetic retinopathy (particularly proliferative diabetic retinopathy), diabetic macular edema, neovascular (exudative) age-related macular degeneration (AMD), including CNV associated with nAMD (neovascular AMD), sequela associated with retinal ischemia, Central Retinal Vein Occlusion (CRVO), posterior segment neovascularization, polypoidal choroidal vasculopathy, proliferative vitreoretinopathy, anterior segment neovascularization, graft-versus-host disease, ocular tumors, corneal graft rejection, and uveitis.

Embodiment 6

A method of treating a mammalian subject having an ocular disease associated with or mediated by CSF-1R, said method comprising administering to the subject an effective amount of Compound (I) as a non-salt or a pharmaceutically acceptable salt thereof.

Embodiment 7

A method of treating an ocular disease associated with or mediated by CSF-1R, said method comprising administering to the subject in need thereof a pharmaceutical composition comprising Compound (I) as a non-salt or a pharmaceutically acceptable salt thereof.

Embodiment 8

A method according to any of the preceding Embodiments, wherein the subject is suffering from an ocular disorder that is selected from the group consisting of: abnormal angiogenesis, choroidal neovascularization (CNV), retinal vascular permeability, retinal edema, diabetic retinopathy (particularly proliferative diabetic retinopathy), diabetic macular edema, neovascular (exudative) age-related macular degeneration (AMD), including CNV associated with nAMD (neovascular AMD), sequela associated with retinal ischemia, Central Retinal Vein Occlusion (CRVO), posterior segment neovascularization, polypoidal choroidal vasculopathy, proliferative vitreoretinopathy, anterior segment neovascularization, graft-versus-host disease, ocular tumors, corneal graft rejection, uveitis, geographic atrophy, dry AMD, wet AMD, glaucoma, and dry eye syndrome (Keratoconjunctivitis Sicca) such as dry eyes resulting from Sjogren's Syndrome.

Embodiment 9

A method according to any of the preceding Embodiments, wherein the subject is suffering from an ocular disorder that is selected from the group consisting of: abnormal angiogenesis, choroidal neovascularization (CNV), retinal vascular permeability, retinal edema, diabetic retinopathy (particularly proliferative diabetic retinopathy), diabetic macular edema, neovascular (exudative) age-related macular degeneration (AMD), including CNV associated with nAMD (neovascular AMD), sequela associated with retinal ischemia, Central Retinal Vein Occlusion (CRVO), posterior segment neovascularization, polypoidal choroidal vasculopathy, proliferative vitreoretinopathy, anterior segment neovascularization, graft-versus-host disease, ocular tumors, corneal graft rejection, and uveitis.

Embodiment 10

A method according to any of the preceding Embodiments, wherein the subject is suffering from an ocular disorder that is selected from the group consisting of: geographic atrophy, dry AMD, wet AMD, glaucoma, and dry eye syndrome (Keratoconjunctivitis Sicca) such as dry eyes resulting from Sjogren's Syndrome.

Embodiment 11

A method according to any of the preceding Embodiments, wherein the subject is suffering from an ocular disorder that is selected from the group consisting of: diabetic retinopathy, corneal neovascularization, noninfectious uveitis, neovascular age-related macular degeneration, and diabetic macular edema.

Embodiment 12

A method according to any of the preceding Embodiments, wherein the compound is a selective inhibitor of CSF-1R.

Embodiment 13

A method according to any of the preceding Embodiments, wherein the method further comprises administering an effective amount of an additional therapeutic agent.

Embodiment 14

A method according to any of the preceding Embodiments, wherein the method further comprises administering an effective amount of an additional therapeutic agent selected from the group consisting of: bevacizumab, ranibizumab, aflibercept, pegpleranib, pegaptanib, conbercept, squalamine, abicipar pegol, PAN-90806, brolucizumab, (S)-5-(6-methyl-5,6,7,8-tetrahydropyrido[3,4-d]pyrimidin-4-yloxy)-N-(5-(1-methylcyclopropyl)-1H-pyrazol-3-yl)-1H-indole-1-carboxamide, 5-(6,7-dihydro-5H-pyrrolo[3,4 d]pyrimidin-4-yloxy)-indole-1-carboxylic acid [5-(1-methyl-cyclopropyl)-2H-pyrazol-3-yl]-amide, 5-(5,6,7,8-tetrahydro-pyrido[3,4-d]pyrimidin-4-yloxy)-indole-1-carboxylic acid [5-(1-methyl-cyclopropyl)-2H-pyrazol-3-yl]-amide, N-(1-methyl-5-(trifluoromethyl)-1H-pyrazol-3-yl)-5-((6-((methylamino)methyl)pyrimidin-4-yl)oxy)-1H-indole-1-carboxamide and REGN2176-3.

Embodiment 15

A method according to any of the preceding Embodiments, wherein the compound as a non-salt or a pharmaceutically acceptable salt thereof or the pharmaceutical composition is administered topically, intravitreally, intracamerally, orally, or intravenously.

Embodiment 16

A method according to any of the preceding Embodiments, wherein the compound as a non-salt or a pharmaceutically acceptable salt thereof or the pharmaceutical composition is administered orally.

Embodiment 17

A method according to any of the preceding Embodiments, wherein the compound as a non-salt or a pharmaceutically acceptable salt thereof or the pharmaceutical composition is administered topically.

Embodiment 18

A method according to any of the preceding Embodiments, wherein the compound as a non-salt or a pharmaceutically acceptable salt thereof or the pharmaceutical composition is administered intravitreally, by injection, or by infusion.

Embodiment 19a

A method according to any of the preceding Embodiments, wherein the compound is Compound (Ia) or a pharmaceutically acceptable salt thereof.

Embodiment 19b

A method according to any of the preceding Embodiments, wherein the compound is Compound (Ib) or a pharmaceutically acceptable salt thereof.

Embodiment 20

A method according to any of the preceding Embodiments, wherein the pharmaceutical composition comprises Compound (Ia) or a pharmaceutically acceptable salt thereof.

Embodiment 21

A method according to any of the preceding Embodiments, wherein the pharmaceutical composition comprises Compound (Ib) or a pharmaceutically acceptable salt thereof.

Embodiment 22

A method according to any of the preceding Embodiments, wherein the compound as a non-salt or a pharmaceutically acceptable salt thereof or the pharmaceutical composition is administered from 1 to 4 times daily.

Embodiment 23

A pharmaceutical composition comprising Compound (I) or a pharmaceutically acceptable salt thereof.

Embodiment 24

A pharmaceutical composition comprising Compound (Ia) or a pharmaceutically acceptable salt thereof.

Embodiment 25

A pharmaceutical composition comprising Compound (Ib) or a pharmaceutically acceptable salt thereof.

Embodiment 26

A pharmaceutical composition according to any of Embodiments 23-25, wherein said composition is an ophthalmically compatible composition.

Embodiment 27

A pharmaceutical composition according to any of Embodiments 23-26, wherein said composition comprises from about 0.01 percent weight/volume to about 5 percent weight/volume of said compound.

Embodiment 28

A pharmaceutical composition according to any of Embodiments 23-27, wherein said composition is a topical composition.

Embodiment 29

A pharmaceutical composition according to any of Embodiments 23-27, wherein said composition is an oral composition.

Embodiment 30

A pharmaceutical composition according to Embodiment 29, wherein said oral composition comprises from 1 to 1000 mg of said compound.

Embodiment 31

A pharmaceutical composition according to any of Embodiments 23-30, comprising Compound (Ia) and/or Compound (Ib) as a non-salt or a pharmaceutically acceptable salt thereof.

Embodiment 32

A pharmaceutical composition according to any of Embodiments 23-31, wherein said oral composition comprises from 1 to 1000 mg of said compound.

Embodiment 33

A pharmaceutical composition according to any of Embodiments 23-32, for treating diabetic retinopathy, diabetic macular edema, or age-related macular degeneration.

Embodiment 34

A pharmaceutical composition according to any of Embodiments 23-33, for treating diabetic retinopathy.

Embodiment 35

A pharmaceutical composition according to any of Embodiments 23-33, for treating diabetic macular edema.

Embodiment 36

A pharmaceutical composition according to any of Embodiments 23-33, for treating age-related macular degeneration.

Embodiment 37

A delivery device including a pharmaceutical composition comprising Compound (I), (Ia), or (Ib) or a pharmaceutically acceptable salt thereof.

Embodiment 38

Compound (I), (Ia), or (Ib) or a pharmaceutically acceptable salt thereof for use in a method of any of the preceding Embodiments.

Embodiment 39

Use of Compound (I), (Ia), or (Ib) or a pharmaceutically acceptable salt thereof for the manufacture of a medicament for use in a method of any of the preceding Embodiments.

As used herein, all percentages are percentages by weight, unless stated otherwise. Unless otherwise indicated, the terms "a" and "an" are taken to mean "one", "at least one" or "one or more". Unless otherwise required by context, singular terms used herein shall include pluralities and plural terms shall include the singular. For clarity, the contents of any patents, patent applications, and references cited throughout this specification are hereby incorporated by reference in their entireties.

Abbreviations

CNV choroidal neovascularization
CTG CellTiter-Glo® Luminescent Cell Viability
DAPI 4',6-diamidino-2-phenylindole
ECL electrochemiluminescence
EDTA ethylenediaminetetraacetic acid
ELISA enzyme-linked immunosorbent assay
FITC fluorescein isothiocyanate
IL-* interleukin *, e.g., IL-8 means interleukin 8
Iba1 ionized calcium binding adaptor molecule 1
i.p. intraperitoneal injection
LPS lipopolysaccharides
MCP-1 monocyte chemoattractant protein 1
MCSF macrophage colony-stimulating factor
MMP9 matrix metallopeptidase 9
PBMC peripheral blood mononuclear cell
pcKit phospho-c-Kit
pCSF-1R phosphorylated CSF-1R
PEC posterior eye cups
pPDGFRβ phosphorylated platelet-derived growth factor receptor β
PDGFRβ platelet-derived growth factor receptor β
q.s. quantum satis or the amount which is enough
RPE retinal pigment epithelium
VEGFa vascular endothelial growth factor A (VEGF-A)

EXAMPLES

The following examples are included to demonstrate embodiments of the present invention. Those of skill in the art will appreciate that changes to the specific embodiments described herein can be made and still obtain a like result without departing from the spirit and scope of the invention.

Example 1—Topical Ophthalmic Preparation

| Ingredients | Concentration (w/v %) |
|---|---|
| Compound (I) | 0.01-2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

Example 2—In Vitro Cell Assays

The procedures detailed below evaluate the effect of Compound (I) on the survival of human PBMC derived monocytes and differentiated macrophages in vitro. In addition, the effect of Compound (I) on cytokine and chemokine production by human macrophages in vitro was evaluated.
Procedures Freshly isolated human PBMCs were used to purify human monocytes by negative selection using an indirect magnetic labeling system. Purified human monocytes were cultured in vitro up to 9 days in the presence of human CSF-1 to differentiation to human macrophages with or without Compound (I) and/or inflammatory stimuli (such as cytokines or LPS) at varies concentrations. Soluble factors such as cytokines (VEGFa, IL-6 etc.) and chemokines (IL-8, MCP-1, MMP9 etc.) in the culture supernatant were measured using commercial ELISA kits. The in vitro survival of human macrophages was measured using a commercially available CellTiter-Glo® system. Most observed results were repeated in multiple donors (n>5).
Results CSF-1 differentiated human monocytes to macrophages after 6 days in culture, and in the absence of CSF-1, human PBMC-derived monocytes did not proliferate and survived in vitro. Compound (I) at 1 and 10 μM concentrations decreased the viability of human macrophages (indicated by CTG values and light microscope pictures) in vitro.

In addition to affecting cell viability at high doses, Compound (I) at a low dose (0.1 μM) downregulated MMP-9 production by human macrophages. As with macrophages, inhibition of CSF-1 signaling by Compound (I) in culture significantly affected monocyte survival, and this effect was concentration dependent (i.e. 0.6 μM or above).

Compound (I) did not affect the survival of fully differentiated, cytokine-polarized human macrophages (M1 or M2). Compound (I) dose-dependently decreased CD206 expression in M2a. However, no Compound (I) dose effect on CD163 expression in M2c macrophages was observed.

Compound (I) challenge increased CSF-1 receptor expression on human monocytes (day 1 to day 3). On day 6 the CSF-1 receptor expression was at its maximum level. Thus, data demonstrates that Compound (I) did not suppress the expression of CSF-1 receptor in human monocytes.

A low dose (0.05 μM) of Compound (I) significantly inhibited MMP-9 (30-50%), MCP-1 (30-70%) and IL-8 (7-90%) production by human monocytes. A dose range (0 to 100 ng/ml) of CSF-1 or IL-34 was tested and macrophage survival positively correlated with increasing dose of CSF-1 or IL-34 with no difference between the 2 factors observed. Accordingly, Compound (I) (from 0.1 to 10 μM) significantly affects both CSF-1 and IL-34 mediated macrophage survival in 4 donors.

Activated human macrophages are a source of VEGFa. Human macrophages produce VEGFa following stimulation with MCSF or IL-34. VEGFa levels significantly decreased in the presence of Compound (I), likely due to less survival of human macrophages.

Example 3—In Vitro Kinase Activity

The ability of Compound (I) to inhibit kinase activity was evaluated by means of in vitro assays. Compound (I) kinase selectivity has been confirmed at the cellular level as assessed by auto-phosphorylation assays (e.g., those known by a skilled artisan or in-house ECL ELISA assays) and BaF3 (a murine interleukin-3 dependent pro-B cell line) proliferation assays (in-house BaF3 panel, see, e.g., Curr. Opin. Oncol. 2007 January; 19(1):55-60). Cellular $EC_{50}$ for pPDGFR3, BAF3-PDGFR3 and pcKit were ≥2 μM and all other BaF3 cell lines were >10 μM, while pCSF-1R and MCSF-dependent proliferation cellular $EC_{50}$ were <71 nM. Additional data from these assays are presented in TABLES 1-3 below.

TABLE 1

| Enzyme | $IC_{50}$ in uM | n |
|---|---|---|
| Abl | >10 | 1 |
| Abl | >10 | 1 |
| Alk | >10 | 1 |
| Aurora_A | >10 | 1 |
| Aurora_A | >10 | 1 |
| Blk | >10 | 1 |
| CamKII alpha | >10 | 1 |
| CDC2_cyclinB | >25 | 1 |
| Cdk7 cyclinH MAT1 | >10 | 1 |
| Chk1 | >10 | 1 |
| Ck1 delta | >10 | 1 |
| Ck1gamma2 | >10 | 1 |
| Ck2alpha1 | >10 | 1 |
| cKit | 3.2 | 11 |
| cKit | >10 | 1 |
| COT | >25 | 3 |
| cRaf | >10 | 1 |
| CSF-1R | 0.001 | 23 |
| Dyrk3 | >10 | 1 |
| Erk1 | >10 | 1 |
| FGFR1 | >25 | 9 |
| FGFR2 | >10 | 1 |
| Flt3 | 9.1 | 6 |
| Flt3 | >10 | 1 |
| Flt3 | >10 | 1 |
| Fyn | >10 | 1 |
| Hck | >10 | 1 |
| Hyl | >10 | 1 |
| IGF-1R | >10 | 1 |
| Insulin RK | >10 | 1 |
| Jak2 | >25 | 1 |
| JNK2alpha2 | >10 | 1 |
| KDR | >25 | 11 |
| KDR | >10 | 1 |
| Lck | >10 | 1 |
| mut_bRaf_V599E | >25 | 5 |
| Nek2 | >10 | 1 |
| PAK1 | >25 | 2 |
| PAK2 | >25 | 3 |
| PAK2 | >10 | 1 |
| PAK4 | >10 | 1 |
| PDGF_RK_alpha | >10 | 1 |
| PDGF_RK_beta | 4.8 | 16 |
| PDK_1 | >25 | 23 |
| PHKG2 | >10 | 1 |

TABLE 1-continued

| Enzyme | IC$_{50}$ in uM | n |
|---|---|---|
| PIK3Calpha | >25 | 9 |
| PIK3Cbeta | >25 | 8 |
| PIK3C_VPS34 | >25 | 4 |
| PIK4Cbeta | >25 | 4 |
| Pim1 | >25 | 7 |
| Pim1 | >10 | 1 |
| Pim2 | >25 | 6 |
| Pim3 | >25 | 11 |
| PKA | >25 | 3 |
| PKC_alpha | >10 | 1 |
| PKC_epsilon | >25 | 3 |
| PKC_theta | >10 | 1 |
| Plk1 | >25 | 6 |
| PHKG2 | >10 | 1 |
| p38alpha | >25 | 1 |
| RAF1_4_CR | >25 | 4 |
| Ron | >10 | 1 |
| ROS | >10 | 1 |
| smMLCK | >10 | 1 |
| Src | >10 | 1 |
| Syk | >10 | 1 |
| TAK1 | >10 | 1 |
| TRKB | >10 | 1 |
| TRKC | >10 | 1 |
| TSSK1 | >10 | 1 |
| ZAP70 | >10 | 1 |

TABLE 2

| Kinase profiling at Invitrogen | % inhibition @ 20 μM | % inhibition @ 5 μM | % inhibition @ 0.5 μM |
|---|---|---|---|
| CSF_1_RK (h) | 95 | 99 | 97 |
| PDGFRKalpha (h) | 55 | 41 | 28 |
| PDGFRKalphaT674I (h) | 45 | 2 | −3 |
| Khs1 (h) | 52 | 27 | 15 |
| Met (h) | 37 | 4 | 0 |
| Syk (h) | −15 | 36 | 32 |

TABLE 3

| Compound | EC50 in uM | Compound | EC50 in uM |
|---|---|---|---|
| BaF-NPM-ALK | >10 | BAF/Tel-RET-Q1/sACP | >10 |
| BaF-Tel-FGFR3 | >10 | BAF/Tel-RON-4.1/sACP | >10 |
| BaF-Tel-IGF1R | >10 | BAF/Tel-MET-3.1/sACP | >10 |
| BaF-Tpr-MET | >10 | BAF/Tel-MER-3.2 | >10 |
| BaF-PTC3-RET | >10 | BAF/Tel-TRKC-Q2/sACP | >10 |
| BaF-Tel-PDGFRbeta | 2.4 | BAF/Tel-TRKB-Q2/sACP | >10 |
| BaF-wt | >10 | BAF/Tel-TRKA-Q.3/sACP | >10 |
| BaF3-Tel-INSR 1.2 | >10 | BAF/Tel-InsR-Q.4/sACP | >10 |
| BaF3-Tel-JAK2; clone1 | >10 | BAF/Tel-IGF1R-FL-N.1/sACP | >10 |
| BaF-Tel-KDR | >10 | | |
| BAF/Tel-EphB2-Q2/sACP | >10 | BAF/Tel-AlK-Q1/sACP | >10 |
| BAF/Tel-EphA3-4.2/sACP | >10 | BAF/Tel-Ros-1.1/sACP | >10 |
| BAF/Tel-Tie1-Q2/sACP | >10 | BAF/Tel-JAK3-S1.2/sACP | >10 |
| BAF/Tel-TIE2-1.2/sACP | >10 | BAF/Tel-JAK2-1.2/sACP | >10 |
| BAF/Tel-PDGFRb-Q2/sACP | 2.4 | BAF/Tel-JAK1-S1.2/sACP | >10 |
| BAF/Tel-FLT3-1.2/sACP | >10 | BAF/Tel-TYK2-1.3/sACP | >10 |
| BAF/Tel-Kit-Q1.2/sACP | >10 | BAF/Tel-FGR-2.1/sACP | >10 |
| BAF/Tel-FMS-1.2/sACP | 1.5 | BAF/Tel-Src-3.1/sACP | >10 |
| BAF/Tel-FLT4-Q2/sACP | >10 | BAF/Tel-Lck-2.1/sACP | >10 |
| BAF/Tel-KDR-Q4/sACP | >10 | BAF/Tel-Lyn-1.2/sACP | >10 |
| BAF/Tel-FLT1-Q1/sACP | >10 | BAF/Tel-BMX-1.2/sACP | >10 |
| BAF/Tel-FGFR3-Q2/sACP | >10 | BAF/Bcr-Abl-Luc/sACP | >10 |
| BAF/Tel-FGFR2-Q1/sACP | >10 | BAF/Tel-ZAP70-1.1/sACP | >10 |
| BAF/Tel-FGFR4-Q4/sACP | >10 | BAF/Tel-Syk-1.1/sACP | >10 |
| | | BAF/bRaf Pim1-1/sACP | >10 |

The experimental data indicate that Compound (I) is selective for CSF-1R, demonstrating 97% inhibition at a concentration of 0.5 μM in one tested assay, and an IC$_{50}$ of 0.001 μM. Tested IC$_{50}$ for Compound (I) relative to VEGF receptor was >25 μM in one tested assay and >10 μM in a second test (as shown in TABLE 1, where KDR=VEGF receptor).

Example 4—In Vivo Model Activity

To investigate the effects of CSF-1R inhibition on ocular angiogenesis and inflammation, Compound (Ia) was assessed in a rodent model of laser-induced choroidal neovascularization (methods below) for effect on blood vessel growth and cellular infiltration after a laser injury. Compound (Ia) was assessed either as a monotherapy or in combination with a suboptimal dose of a VEGF antibody.

In one experiment, Compound (Ia) or vehicle was dosed orally at 30, 100 or 200 mg/kg starting about 1 hour before laser and continued administration daily until the day before tissue harvest.

In a second experiment, mice were dosed daily with 50 mg/kg of Compound (Ia) and with i.p. injections of a mouse anti-VEGF antibody at a dose of 0.3 mg/kg at day 0, 2 and 4. Other groups of mice in the experiment were dosed with monotherapy of Compound (Ia) or the anti-VEGF antibody at higher doses.

Methods

Laser Photocoagulation

Mouse pupils were dilated with one drop (~40 μL) of 1% cyclopentolate. Just before anesthesia, pupil dilation was maximized with an additional drop of phenylephrine (usually 10% but occasionally 2.5% depending upon availability). Mice were then anesthetized with an i.p. injection of a mixture of ketamine and xylazine at doses of 80-100 mg/kg and 5-10 mg/kg, respectively. Prior to laser pulse application, each eye was anesthetized with topical 0.5% proparacaine. Lubricating eyedrops (Genteal® Alcon Laboratories, Fort Worth, Tex.) on a glass cover slip were applied to the cornea, and the retina was viewed through a slit lamp microscope. Each laser pulse was applied approximately 0.5 to 1 mm from the optic nerve; single pulses in each of three separate locations were applied to each eye for a total of six laser photocoagulation sites for each mouse. The pulses were from a green laser (wavelength=532 nm; Oculight® GLx Mountain View, Calif.) and had a duration of 30 milliseconds, a power of 120 milliwatts, and a spot size of 100 microns. A successful laser pulse generated a yellow vaporization bubble which correlated with a rupture of Bruch's membrane. When a vaporization bubble did not form (incidence is <1% of laser pulse applications), one additional laser pulse could be administered to the same spot. For each eye, a maximum of four laser pulses were allowed to generate 3 lesions. After the application of laser burns to both eyes, antibiotic ointment (Tobramycin or Neomycin ophthalmic ointment) was applied to both eyes.

Tissue Processing, Imaging and CNV Area Quantification

Analysis of neovascularization was completed on tissues harvested 7 days after laser photocoagulation. On day 7, 0.1 ml of a 5 mg/ml solution of FITC concanavalin-A (Vector Laboratories, Burlingame, Calif.) was injected intravenously (i.v.) to fluorescently label vascular endothelium. Animals were euthanized 15-30 minutes later with inhaled carbon dioxide. Eyes were enucleated and fixed in 4% paraformaldehyde (Vector Laboratories, Burlingame, Calif.) for approximately 60 minutes at room temperature, and then the fixative was replaced with PBS. Each eye was assigned a randomized number to mask the samples for the remainder of the analysis. Posterior segments were isolated and retinas were removed. The posterior eye cups (PEC) which included the retinal pigment epithelium (RPE), the choroid, and the sclera, were flat-mounted onto microscope slides after making 3 or 4 radial cuts. Fluorescent images of each CNV lesion were photographed with an Axiocam MR3 camera on an Axio Image M1 microscope (Carl Zeiss Microscopy, Thornwood, N.Y.). CNV area was quantified using a semi-automated analysis program (Axiovision software version 4.5, Carl Zeiss Microscopy) that outlined the fluorescent blood vessels. Image capture, CNV area measurement and exclusions were performed on randomized samples or data by scientists masked to the treatment group. Exclusion criteria were applied as previously reported.

Cellular Infiltration Assay

Cellular infiltration into the retina, the PEC or the CNV lesion was assessed after laser application. Eyes were fixed with 4% Paraformaldehyde for ~90 minutes. After fixation, whole eyes were dissected into the retina and PEC. Tissues were blocked in phosphate buffered saline (PBS) with 1% Bovine Serum Albumin (BSA) (EMD Millipore, Billerica, Mass.) for 1-2 hours. Retinas were incubated overnight with rat anti-mouse F4/80 (Abcam, Cambridge, Mass.) 1:1000 in staining buffer (1% BSA and 0.5% Triton-X 100, MP Biomedicals, Santa Ana, Calif.) to label macrophages. The PEC was incubated overnight with rabbit anti-mouse Iba1 (Wako Chemicals, Cambridge, Mass.) 1:1,000 to label microglia and/or macrophages, and biotin-Ly-6G/C, also known as Gr1, (Biolegend, San Diego, Calif.) 1:1,000 in staining buffer to label neutrophils. Tissues were washed with washing buffer (1% BSA in PBS) 3 times each for 20 minutes. Retinas were then incubated for 2 hours with anti-rat alexa fluor 594 (Thermo, A-11007) 1:1,000 in staining buffer, and the PEC incubated for 2 hours with anti-rabbit alexa fluor 488 (Thermo, A-21206) 1:1,000 and Streptavidin Alexa fluor 594 (Thermo, S32356) in staining buffer. Tissues were then washed with washing buffer 3 times each for 15 minutes. Tissues were flat mounted with Vectashield with DAPI (Vector Laboratories, Burlingame, Calif.).

Imaging

Flat mounted retinas and PEC were imaged with a Zeiss Axio Imager M1 fluorescent camera at different magnifications. To visualize the infiltrating Iba1+ cells in the PEC and CNV, images at 5× magnification of the PEC were captured centered on the optic nerve covering approximately 70% of the tissue. Images of Gr-1+ neutrophils in CNV lesions were captured at 20× magnification. Images of F4/80+ macrophages on the vitreal side of the retina were captured at 10× magnification with 3 non-overlapping images collected per retina with one image centered on the optic nerve, a second and third image on retinal petals peripheral to the optic nerve, the 3 images covering ~40% of the retina.

Peripheral Cell Count

Iba1+ cells in the PEC peripheral to the CNV lesion were counted using a different semi-automatic MatLab code. The code identifies candidate individual cells (small areas of high pixel intensity). The operator is then presented with masked, randomized images and allowed the functionality to remove miscellaneous fluorescence (false positive) and add missed cells (false negative) to the analysis. Confluent microglia cells and CNV lesions were excluded from the quantification analysis. In a study, each assessed condition consisted of 10 eyes from 5 mice and would typically yield 10 data points. Whole eyes were excluded from the analysis if large hemorrhage or anatomical damage from dissection covered more than 10% of the tissue. F4/80+ cells in the retina were counted using a similar semi-automatic MatLab code and followed the same procedure as above. Whole eyes were excluded from the analysis if large hemorrhage or anatomical damage from dissection covered more than 10% of the tissue.

Results

Compound (Ia) demonstrated dose dependent inhibition of CNV area, with a 75% reduction in area compared to mice dosed with vehicle, as shown in FIG. 1.

Figure 2:
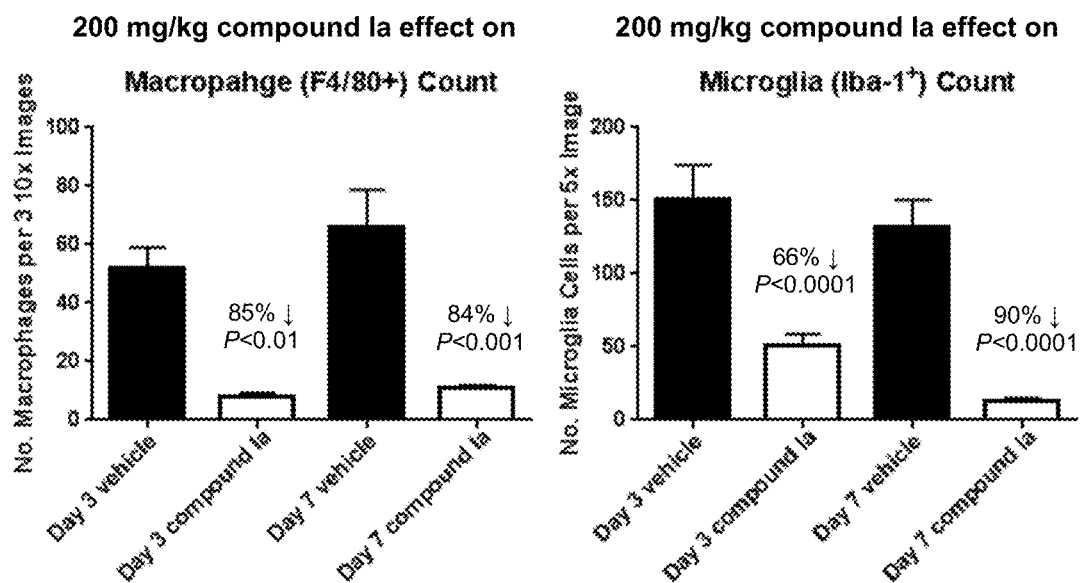
FIG. 2 shows bar graphs comparing macrophage and microglia cell counts assayed after photocoagulation in a rodent model of laser-induced choroidal neovascularization.

Compound (Ia) demonstrated marked inhibition of retinal F4/80+ cells (83-84% reduction in macrophages) and sub-retinal Iba1+ cells (66-99% reduction in microglia) as shown in FIG. 2 when dosed at 200 mg/kg.

Figure 3:
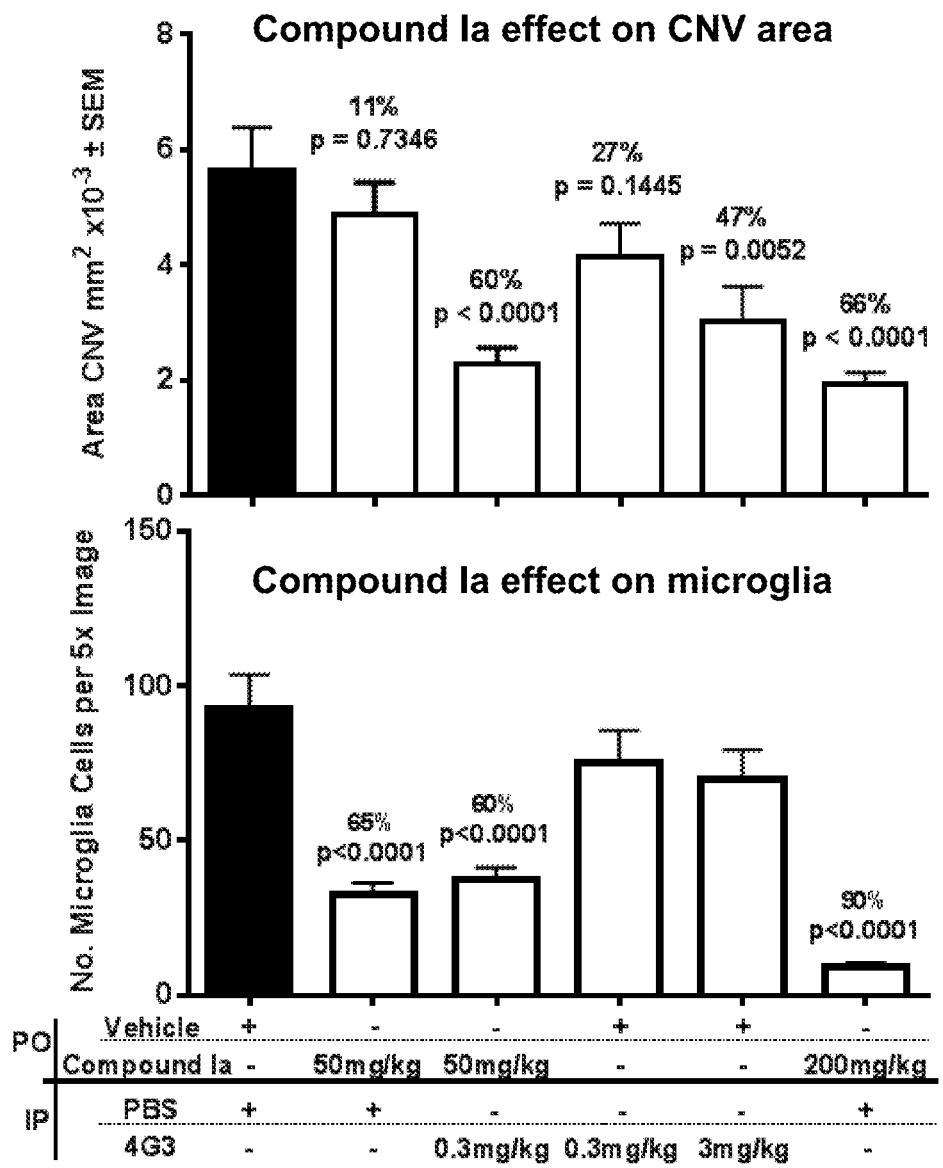
FIG. 3 shows bar graphs comparing neovascularization area data, as well as macrophage and microglia cell counts assayed after photocoagulation in a rodent model of laser-induced choroidal neovascularization.

As shown in FIG. 3, mice dosed with Compound (Ia) and anti-VEGF antibody (designated 4G3) in combination demonstrated an additive effect on inhibition of CNV area. Mice dosed with Compound (Ia) at 50 and 200 mg/kg had significantly reduced microglia and macrophages in the subretinal space and retina. No statistically significant effect on cellular count was observed in mice treated with anti-VEGF monotherapy.

Example 5—In Vivo Model Activity

To investigate the effects of CSF-1R inhibition on inflammation, Compound (Ia) was assessed in CX3CR1-GFP reporter mice (which report on macrophage and microglia). The presence of macrophages in areas around the ciliary body in the front of the eye (but not in the cornea) was examined and confirmed by anti-GFP immunohistochemistry staining (see panels (a) and (b) in FIG. 4). The arrow-indicated dots are the positive stained macrophage cells).

Figure 4:
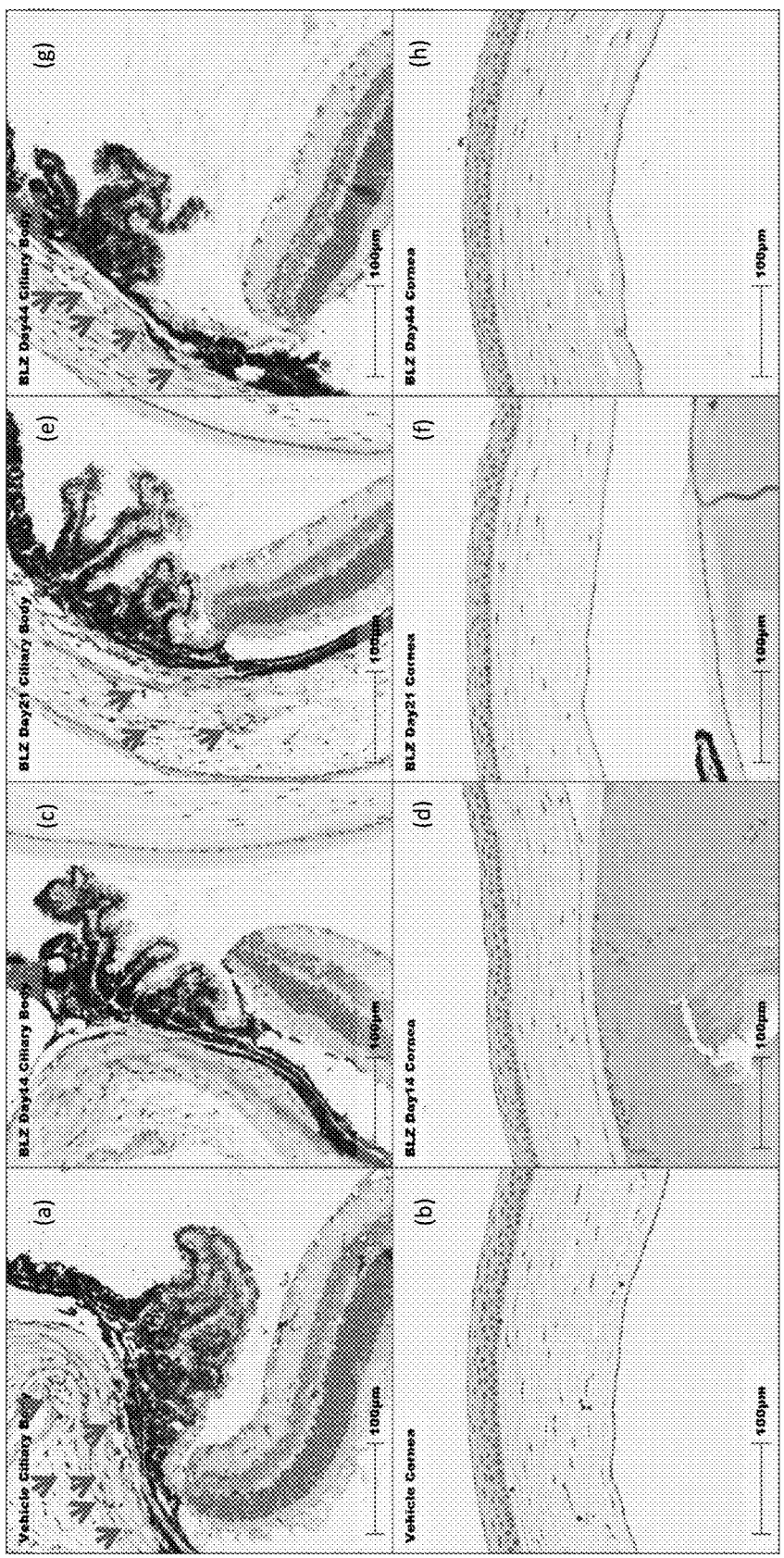
FIG. 4 is a series of micrographs showing the effects of Compound (Ia) on macrophages in areas around the ciliary body in a rodent model. The dots indicated by arrows in panels (a), (e) and (g) are the stained macrophage cells. Panels (a) and (b) shows respectively a part of the ciliary body and cornea of a vehicle-treated mouse; panels (c)-(h) respectively shows a part of the ciliary body and cornea of a Compound (Ia)-treated mouse at day 14, 21, and 44 after daily oral administration of 200 mg/kg Compound (Ia) (referred to as "BLZ" in FIG. 4) for 14 days.

In this experiment, mice was treated with a salt of Compound (Ia) orally at 200 mg/kg daily for 14 days and immediately examined for the presence of macrophages (see panels (c) and (d) in FIG. 4). As shown in FIG. 4, macrophages were depleted in areas around the ciliary body on day 14. Macrophages started to return on day 21 (panels (e) and (f)) and were almost back to steady state on day 44 (panels (g) and (h)).

The results indicate that macrophages reside in the ocular surface tissues of mice and that regulation of macrophages by Compound (Ia) or a salt thereof may turn off the inflammatory immune response responsible for dry eye disease and therefore alleviating or treating dry eye or symptoms thereof.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the invention that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein. The claims should not be read as limited to the described order or elements unless stated to that effect. It should be understood that various changes in form and detail may be made without departing from the scope of the appended claims.

What is claimed is:

1. A method of treating an ocular disease or disorder that is mediated by CSF-1R comprising:
   administering to a subject in need thereof an effective amount of Compound (I):

(I)

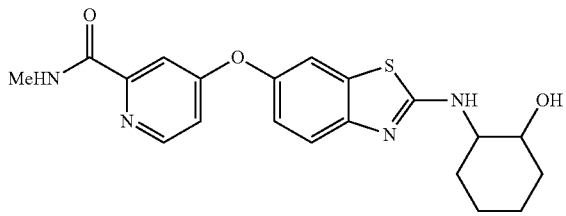

as a non-salt or a pharmaceutically acceptable salt thereof.

2. The method of claim 1, wherein said ocular disease or disorder is an ocular neovascular disease.

3. The method of claim 1, wherein said ocular disease is selected from the group consisting of:
   noninfectious uveitis, dry eye syndrome (Keratoconjunctivitis Sicca), corneal neovascularization, glaucoma, abnormal angiogenesis, choroidal neovascularization (CNV), retinal vascular permeability, retinal edema, diabetic retinopathy, diabetic macular edema, neovascular age-related macular degeneration (AMD), sequela associated with retinal ischemia, central retinal vein occlusion (CRVO), posterior segment neovascularization, polypoidal choroidal vasculopathy, proliferative vitreoretinopathy, anterior segment neovascularization, graft-versus-host disease, ocular tumors, corneal graft rejection, and uveitis.

4. The method of claim 1, wherein Compound (I) or the pharmaceutically acceptable salt thereof is administered topically, intravitreally, intracamerally, orally, or intravenously.

5. The method of claim 1, wherein Compound (I) or the pharmaceutically acceptable salt thereof is administered from 1 to 4 times daily.

6. The method of claim 1, wherein the method further comprises administering an effective amount of an additional therapeutic agent selected from the group consisting of: bevacizumab, ranibizumab, aflibercept, pegpleranib, pegaptanib, conbercept, squalamine, abicipar pegol, PAN-90806, RTH258, (S)-5-(6-methyl-5,6,7,8-tetrahydropyrido[3,4-d]pyrimidin-4-yloxy)-N-(5-(1-methylcyclopropyl)-1H-pyrazol-3-yl)-1H-indole-1-carboxamide, 5-(6,7-dihydro-5H-pyrrolo[3,4 d]pyrimidin-4-yloxy)-indole-1-carboxylic acid [5-(1-methyl-cyclopropyl)-2H-pyrazol-3-yl]-amide, 5-(5,6,7,8-tetrahydro-pyrido[3,4-d]pyrimidin-4-yloxy)-indole-1-carboxylic acid [5-(1-methyl-cyclopropyl)-2H-pyrazol-3-yl]-amide, N-(1-methyl-5-(trifluoromethyl)-1H-pyrazol-3-yl)-5-((6-((methylamino)methyl)pyrimidin-4-yl)oxy)-1H-indole-1-carboxamide and REGN2176-3.

7. The method of claim 1, wherein Compound (I) comprises:

Compound (Ia)

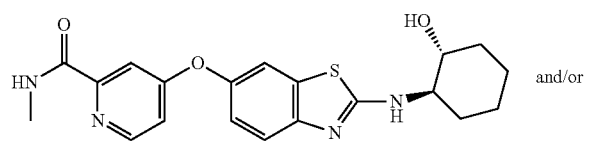

and/or

Compound (Ib)

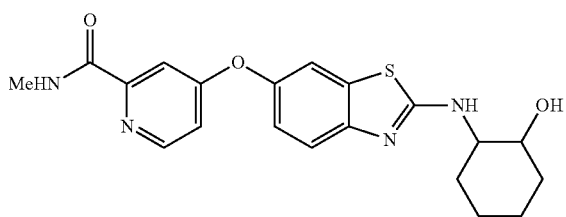

.

8. A method of treating diabetic retinopathy, diabetic macular edema, or age-related macular degeneration, in a mammalian subject suffering therefrom, said method comprising administering to the subject an effective amount of Compound (I):

(I)

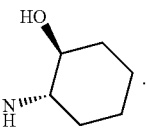

as a non-salt or a pharmaceutically acceptable salt thereof in a pharmaceutical composition.

9. The method of claim 8, wherein said composition is an ophthalmic composition.

10. The method of claim 9, wherein said composition comprises from about 0.01 percent weight/volume to about 5 percent weight/volume of Compound (I).

11. The method of claim 9, wherein said composition is a topical ophthalmic composition.

12. The method of claim 8, wherein said composition is administered topically, intravitreally, intracamerally, orally, or intravenously.

13. The method of claim 8, wherein said composition is an oral composition.

14. The method of claim 13, wherein said oral composition comprises from 1 to 1000 mg of Compound (I).

15. The method of claim 8, wherein said composition comprises:

Compound (Ia)

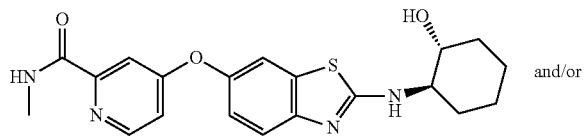

and/or

Compound (Ib)

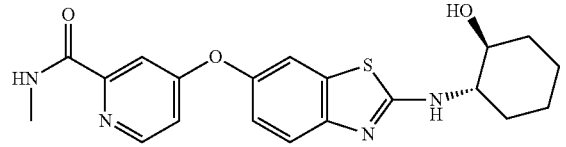

or a pharmaceutically acceptable salt thereof.

16. The method of claim 1, wherein the subject is a human.

17. The method of claim 1, wherein the Compound (I) is administered to the subject topically or orally.

18. The method of claim 1, wherein the ocular disease or disorder is diabetic retinopathy, diabetic macular edema, or age-related macular degeneration.

19. The method of claim 8, wherein the mammalian subject is a human.

* * * * *